United States Patent

O'Neil et al.

[11] Patent Number: 6,053,945
[45] Date of Patent: *Apr. 25, 2000

[54] JOINT PROSTHESIS HAVING CONTROLLED ROTATION

[75] Inventors: Michael J. O'Neil, West Barnstable; Arnold Oyola, Taunton; Edward J. Cheal, Duxbury, all of Mass.

[73] Assignee: Johnson & Johnson Professional, Inc., Raynham, Mass.

[*] Notice: This patent is subject to a terminal disclaimer.

[21] Appl. No.: 08/936,925

[22] Filed: Sep. 25, 1997

[51] Int. Cl.⁷ ..................................................... A61F 2/64

[52] U.S. Cl. ................................................. 623/20; 638/18

[58] Field of Search .................................. 623/18, 20, 22

[56] References Cited

U.S. PATENT DOCUMENTS

| | | |
|---|---|---|
| 4,136,405 | 1/1979 | Pastrick et al. ............................ 623/20 |
| 4,219,893 | 9/1980 | Noiles ...................................... 3/1.911 |
| 4,301,553 | 11/1981 | Noiles ...................................... 3/1.911 |
| 4,538,305 | 9/1985 | Engelbrecht et al. ..................... 623/20 |
| 4,634,444 | 1/1987 | Noiles ...................................... 623/20 |
| 4,769,039 | 9/1988 | Horber ...................................... 623/20 |
| 4,790,853 | 12/1988 | Englbrecht et al. ....................... 623/20 |
| 4,888,021 | 12/1989 | Forte et al. ................................ 623/20 |
| 4,936,847 | 6/1990 | Manginelli ................................. 623/23 |
| 4,950,297 | 8/1990 | Elloy et al. ................................ 623/20 |
| 5,011,496 | 4/1991 | Forte et al. ................................ 623/20 |
| 5,026,399 | 6/1991 | Engelbrecht et al. ..................... 623/18 |
| 5,059,216 | 10/1991 | Winters ..................................... 623/20 |
| 5,071,438 | 12/1991 | Jones et al. ............................... 623/20 |
| 5,080,675 | 1/1992 | Lawes et al. ............................. 623/20 |
| 5,171,283 | 12/1992 | Pappas et al. ............................ 623/20 |
| 5,370,699 | 12/1994 | Hood et al. ............................... 623/20 |
| 5,370,701 | 12/1994 | Finn .......................................... 623/20 |
| 5,387,240 | 2/1995 | Pottenger et al. ........................ 623/20 |
| 5,395,401 | 3/1995 | Bahler ...................................... 623/20 |
| 5,413,608 | 5/1995 | Keller ....................................... 623/20 |
| 5,489,311 | 2/1996 | Cipolletti ................................. 623/20 |
| 5,609,644 | 3/1997 | Ashby et al. ............................. 623/18 |
| 5,683,468 | 11/1997 | Pappas ..................................... 623/20 |

FOREIGN PATENT DOCUMENTS

| | | | |
|---|---|---|---|
| 0018364 | 11/1980 | European Pat. Off. .......... | A61F 1/00 |
| 0046926 | 3/1982 | European Pat. Off. .......... | A61F 1/03 |
| 0183670 | 6/1986 | European Pat. Off. .......... | A61F 2/38 |
| 0346183 | 12/1989 | European Pat. Off. .......... | A61F 2/38 |
| 0519872 | 12/1992 | European Pat. Off. .......... | A61F 2/38 |
| 0529408 | 3/1993 | European Pat. Off. .......... | A61F 2/38 |
| 0568756 | 11/1993 | European Pat. Off. .......... | A61F 2/38 |
| 0592750 | 4/1994 | European Pat. Off. .......... | A61F 2/38 |
| 0626156 | 11/1994 | European Pat. Off. .......... | A61F 2/38 |
| 0627202 | 12/1994 | European Pat. Off. .......... | A61F 2/38 |
| 0636353 | 2/1995 | European Pat. Off. .......... | A61F 2/38 |
| 0678286 | 10/1995 | European Pat. Off. .......... | A61F 2/38 |
| 0682925 | 11/1995 | European Pat. Off. .......... | A61F 2/38 |
| 0732091 | 9/1996 | European Pat. Off. .......... | A61F 2/38 |
| 2726174 | 5/1996 | France .............................. | A61F 2/38 |
| 2728782 | 7/1996 | France .............................. | A61F 2/38 |
| 3136636 | 3/1983 | Germany .......................... | A61F 1/03 |
| 9517860 | 7/1995 | WIPO ............................... | A61F 2/38 |
| 9525484 | 9/1995 | WIPO ............................... | A61F 2/38 |
| 9530390 | 11/1995 | WIPO ............................... | A61F 2/38 |
| 96/00538 | 1/1996 | WIPO ............................... | 623/20 |
| 9600538 | 1/1996 | WIPO ............................... | A61F 2/38 |
| 9603097 | 2/1996 | WIPO ............................... | A61F 2/38 |

OTHER PUBLICATIONS

DePuy ®, LCS AP Glide™, Clinical Evaluation, May. 1995, 11 pp.

*Primary Examiner*—Bruce E. Snow
*Attorney, Agent, or Firm*—Nutter, McClennen & Fish, LLP

[57] ABSTRACT

A joint prosthesis system includes first and second components that are joinable to each other in a manner to inhibit the rotation of the second component relative to the first component. The prosthesis system includes a rotation-inhibiting mechanism that has at least circumferential groove formed in one of a portion of the first component and a portion of the second component and at least one rib formed on the other of the first component and the second component. In one embodiment the rib may be eccentric, and the groove and the rib are matable with each other upon mounting of the second component within the first component.

16 Claims, 9 Drawing Sheets

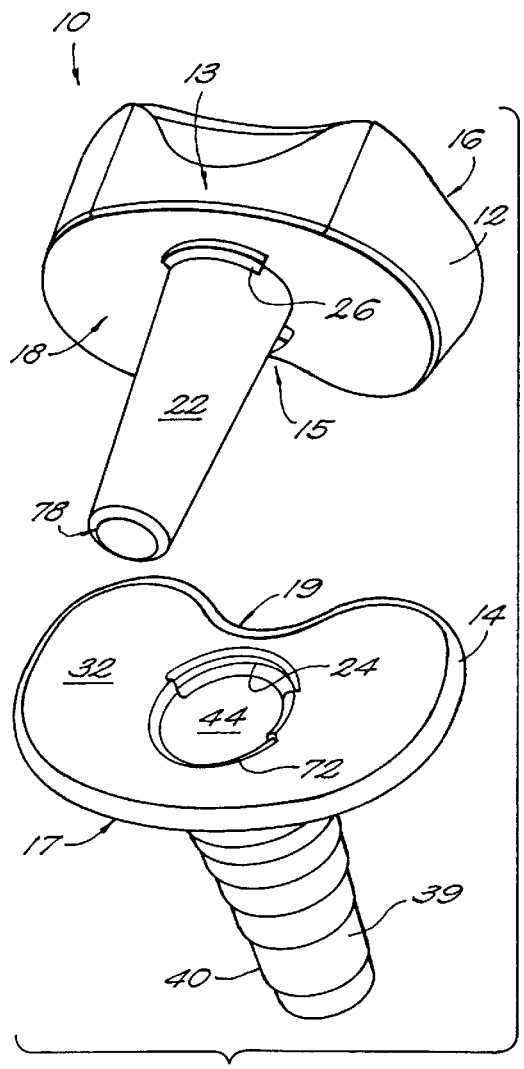
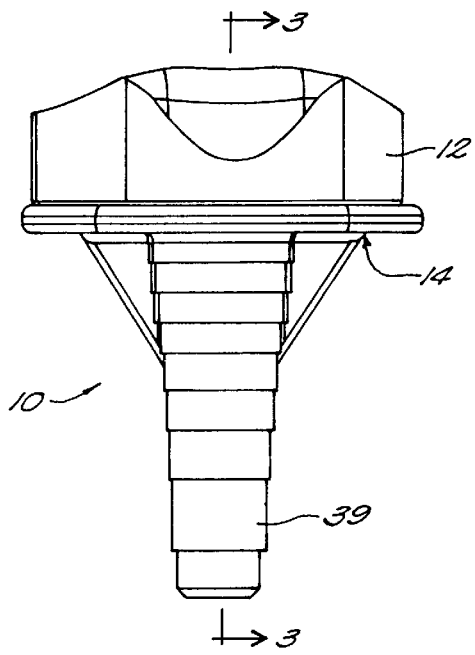
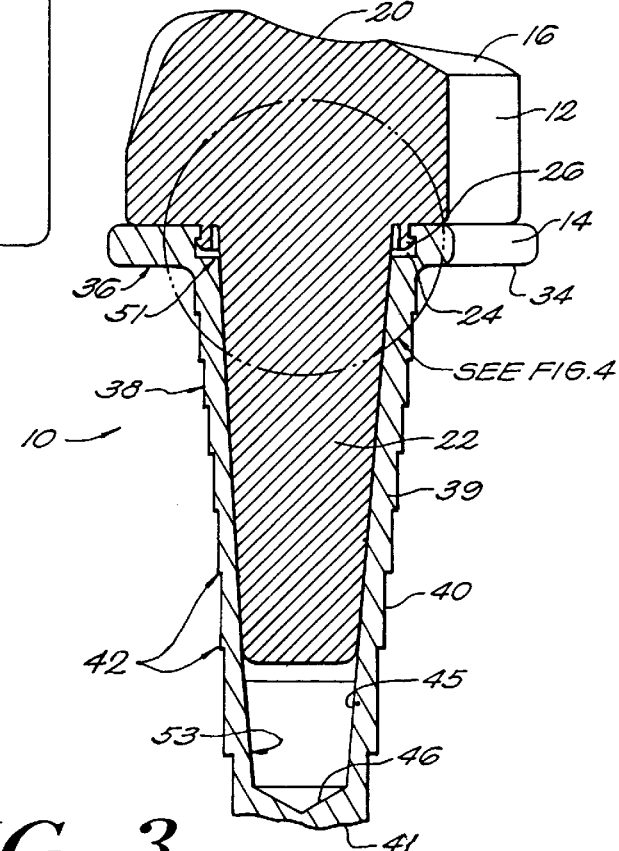
FIG. 1
FIG. 2
FIG. 3

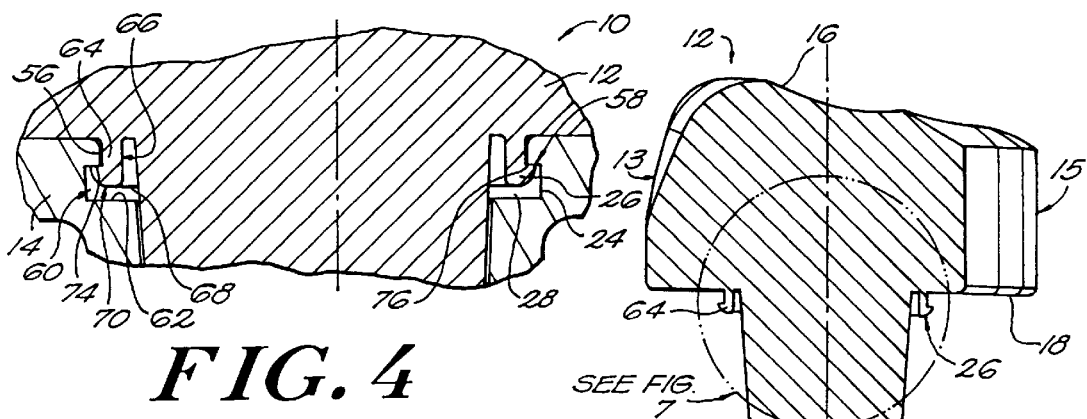
FIG. 4
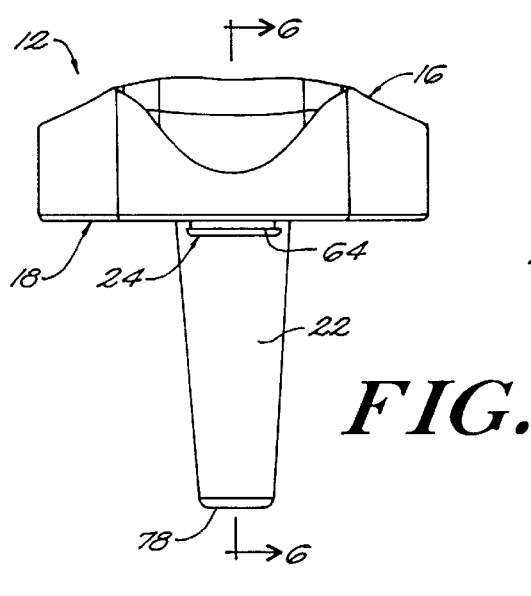
FIG. 5
FIG. 6
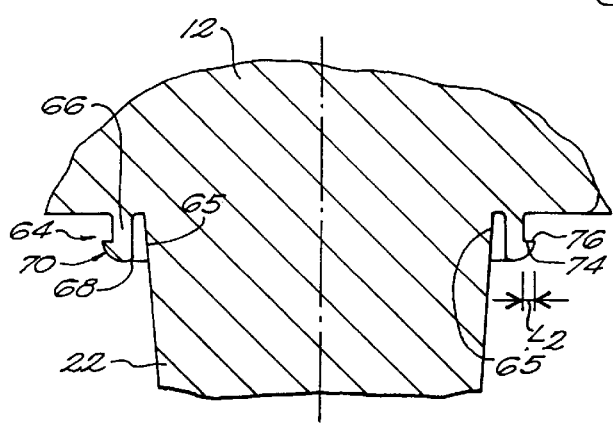
FIG. 7
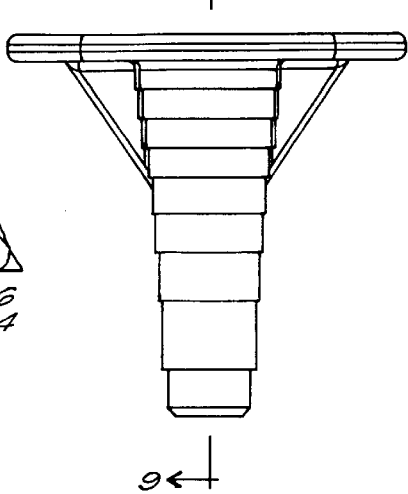
FIG. 8

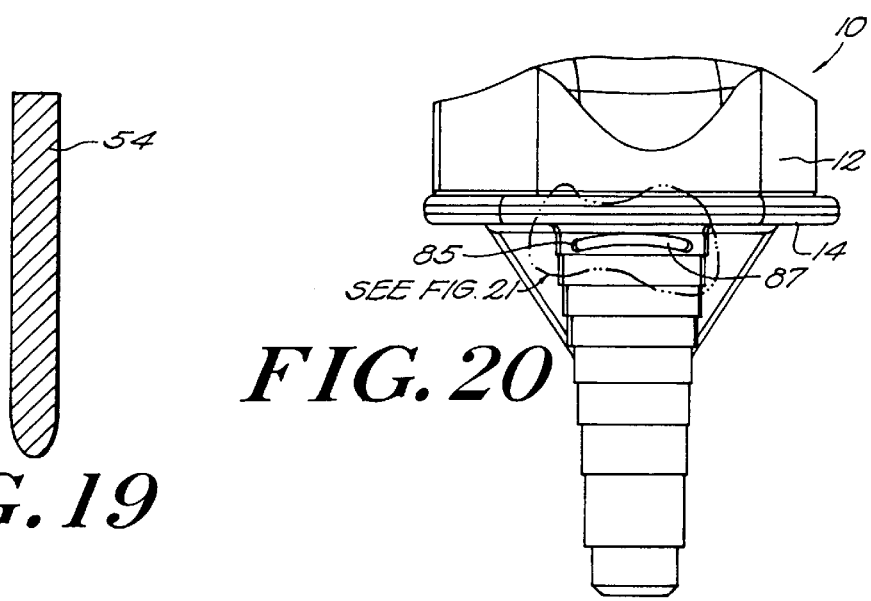
FIG. 19
FIG. 20
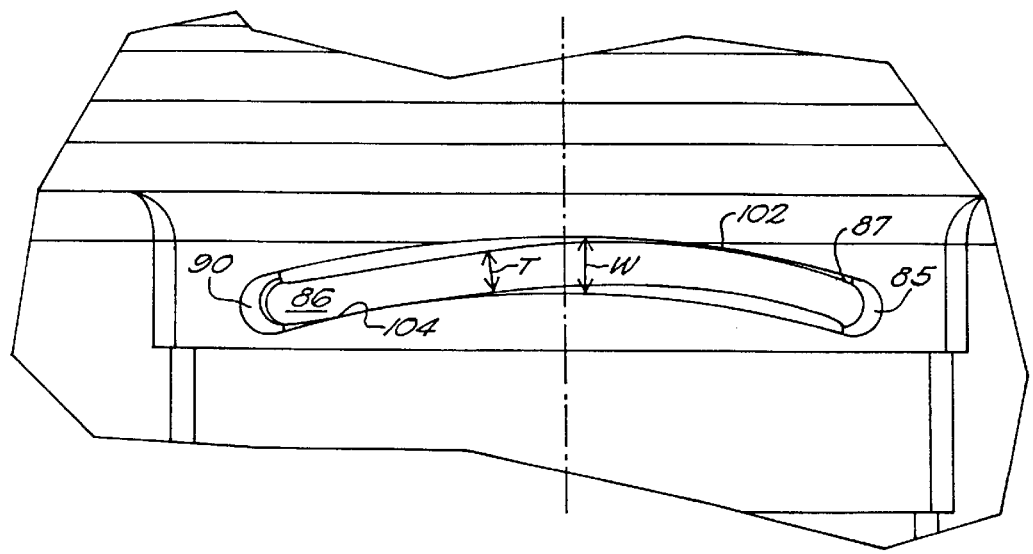
FIG. 21
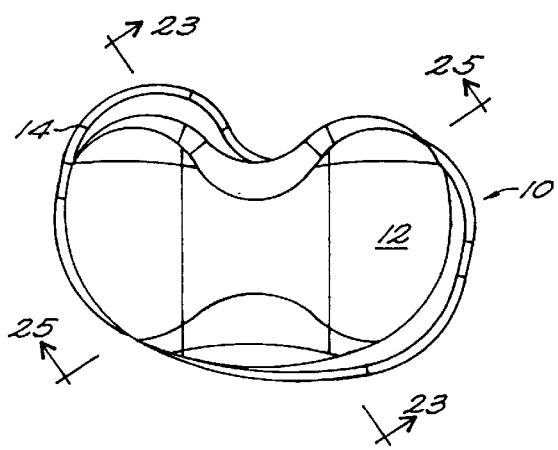
FIG. 22

JOINT PROSTHESIS HAVING CONTROLLED ROTATION

CROSS REFERENCE TO RELATED APPLICATIONS

Not applicable.

STATEMENT REGARDING FEDERALLY SPONSORED RESEARCH

Not applicable.

BACKGROUND OF THE INVENTION

The invention relates to joint prostheses. More particularly, the invention is directed to tibial components of knee joint prostheses that have a tibial bearing insert that is axially secured to a tibial tray, and rotatable with respect to the tibial tray upon which it is mounted.

Joint replacement surgery is quite common and enables many individuals to function normally when otherwise it would not be possible to do so. Artificial joints are normally composed of metallic, ceramic and/or plastic components that are fixed to existing bone.

Knee arthoplasty is a well known surgical procedure by which a diseased and/or damaged natural knee joint is replaced with a prosthetic knee joint. Typical knee protheses include a femoral component, a patella component, a tibial tray or plateau, and a tibial bearing insert. The femoral component generally includes a pair of laterally spaced apart condylar portions, the distal surfaces of which articulate with complementary condylar elements formed in a tibial bearing insert.

The tibial tray is mounted within the tibia of a patient. Typically, the tibial bearing insert, which is usually made of ultra high molecular weight polyethylene (UHMWPE) is mounted upon the superior surface of the tibial tray. Load and stress are placed upon the knee prosthesis, and particularly on the tibial bearing insert, during normal daily use. These forces may lead to the displacement or dislocation of the insert from the tibial tray. To accommodate these forces, and to reduce the chances for dislocation, some tibial components of knee prostheses have been designed to allow rotation of the tibial bearing insert relative to the proximal or superior surface of the tibial tray, about the longitudinal axis of the prosthesis. Such rotation, when controlled, can increase the contact area between the femoral condyles and the tibial bearing insert throughout the range of knee motion, thus reducing stress on the tibial bearing insert.

Some knee prosthesis tibial components accommodate insert rotation without providing axial securement of the tibial bearing insert within the tibial tray. That is, some tibial bearing inserts that are able to rotate with respect to a tibial tray are not fully secured within the tibial tray. Certain forces to which the knee is subjected, particularly forces with axially directed components, may cause the tibial bearing insert to separate from the tibial tray.

Various designs for rotatable tibial components of knee joint prostheses are known in the art. For example, U.S. Pat. No. 4,219,893 (Noiles) and U.S. Pat. No. 4,301,553 (Noiles) disclose knee joint prostheses in which the tibial component comprises a tibial tray having a bearing surface with a recessed region within which the tibial bearing insert may rest. A sufficient clearance is provided in the bearing surface of the tibial tray to allow some medial-lateral rotation of the tibial bearing insert with respect to the tray. Other patents that disclose tibial components of knee joint prostheses in which a tibial bearing insert is rotatable with respect to the tibial tray are disclosed in U.S. Pat. Nos. 5,059,216 (Winters); 5,071,438 (Jones et al); 5,171,283 (Pappas et al); and 5,489,311 (Cipolletti).

Despite the existing designs for knee joint prostheses having a rotatable tibial component, there remains a need for prostheses that allow rotation of the tibial bearing insert to accommodate the stresses placed upon the knee. At the same time, such tibial bearing inserts should possess sufficient axial securement so as to decrease or eliminate the possibility of subluxation of the tibial bearing insert.

SUMMARY OF THE INVENTION

The invention is directed to a joint prosthesis system having a first component and a second component, wherein the second component is rotatable with respect to the first component while maintaining axial securement of the second component to the first component. The term "axial securement" refers to the ability of the second component to resist withdrawal or separation from the first component when subjected to a separation force. In a preferred embodiment, the joint prosthesis system is a knee joint prosthesis in which the first component is a tibial tray and the second component is a tibial bearing insert for use in knee joint prostheses.

The prosthesis system of the invention includes a first component (e.g., a tibial tray) having a superior mounting surface and an inferior bone contacting surface. The bone contacting surface includes an anchor stem having outer, implantable side and distal walls. Preferably, a cavity is formed in the mounting surface and extends into the anchor stem. This cavity is defined by an inner side and distal walls.

A second component (e.g., a tibial bearing insert) of the prosthesis system has a superior articulation surface and an inferior surface that is mountable within the cavity of the first component. The inferior surface includes a mating stem that is mountable within the cavity of the first component and which has a size and shape complementary to the cavity.

The prosthesis system also includes a securing mechanism that has at least one first surface feature (e.g., a negative surface feature) located on the interior side wall of the first component and at least one second surface feature (e.g., a positive surface feature) located on the second component. The first and second surface features are engageable so that, upon engagement, the second component is rotatable with respect to the first component while remaining axially secured to the first component. In one embodiment, the first surface feature and the second surface feature are adapted and dimensioned to engage and form a snap fit arrangement.

The prosthesis system may also include an axial bore formed in the superior bearing surface of the second component that extends into the mating stem of the second component. The bore has a size and dimensions sufficient to receive an elongate reinforcement pin that can be mounted within the bore. In a further embodiment, insertion of the reinforcement pin can effect engagement of the positive and negative surface features.

In another embodiment the positive surface feature is an eccentrically shaped rib adapted to mate with a negative surface feature (e.g., a groove). The rib enables one prosthesis component to mate with another prosthesis component to provide axial securement and controlled rotation of the one component with respect to the other component.

BRIEF DESCRIPTION OF THE DRAWINGS

FIG. 1 is exploded perspective view of two components of a knee joint prosthesis system according to the present invention.

FIG. 2 is a front view of the assembled components shown in FIG. 1.

FIG. 3 is a side sectional view of the assembled components of the prosthesis system shown in FIG. 2, at line 3—3.

FIG. 4 is a detail view of a portion "A" of FIG. 3.

FIG. 5 is a front view of a tibial bearing insert according to the present invention.

FIG. 6 is a sectional view of the tibial bearing insert of FIG. 5, at line 6—6.

FIG. 7 is a detail view of portion "B" of the tibial bearing insert of FIG. 6.

FIG. 8 is a front view of a tibial tray according to the present invention.

FIG. 19 is a sectional view of a reinforcement pin.

FIG. 20 is a front view, with partial cutaway, of a prothesis system according to an alternative embodiment of the invention.

FIG. 21 is a detail view of Detail A of the system of FIG. 20.

FIG. 22 is a top view of the prosthesis system of FIG. 20 with the tibial bearing insert rotated approximately 5° with respect to the tibial tray.

DETAILED DESCRIPTION OF THE INVENTION

Figure 11:
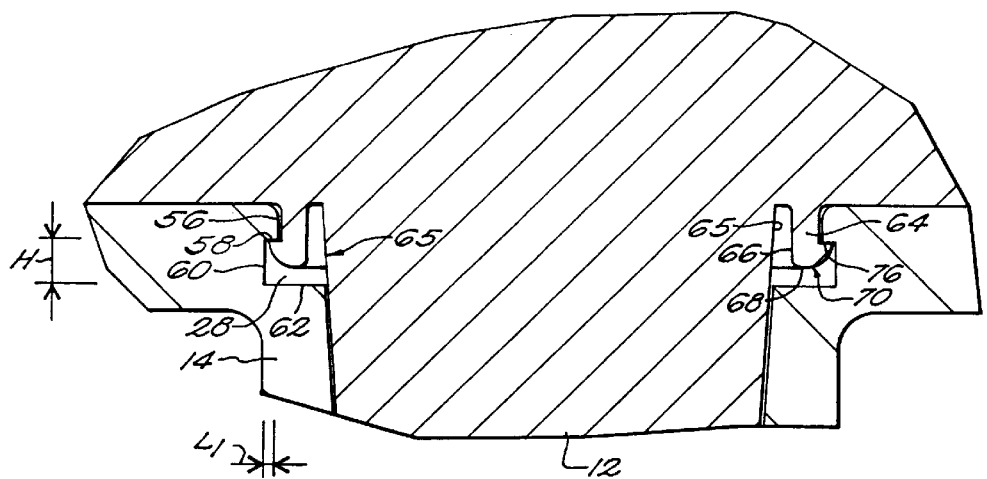
FIG. 11 is a partial sectional view of the prosthesis system of the invention in which tibial bearing insert is rotated approximately 4° relative to the tibial tray.
Figure 9:
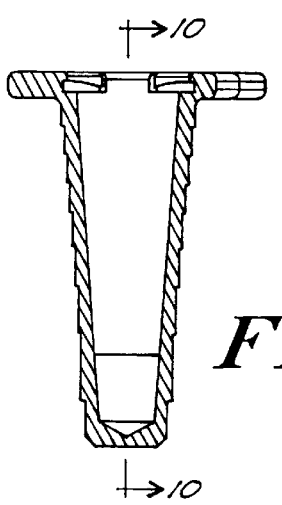
FIG. 9 is a front sectional view of the tibial tray of FIG. 8, at line 9—9.
Figure 10:
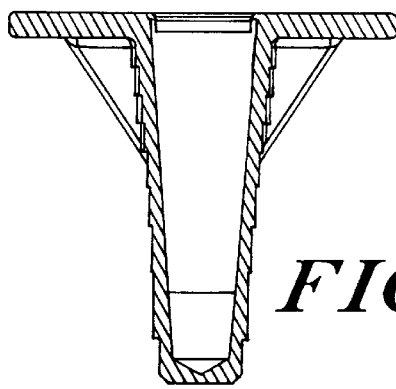
FIG. 10 is a side sectional view of the tibial tray of FIG. 9, at line 10—10.

The invention provides a prosthesis system 10 that has first and second components that can be axially secured to one another while maintaining the ability of one component to rotate with respect to the other. For purposes of illustration the system 10 is shown as the tibial component of a knee joint prosthesis. It is understood, however, that the invention is applicable to other prostheses.

Referring to FIGS. 1 and 2, the system 10 includes a first component in the form of a tibial tray 14, upon which is mounted a second component, i.e., tibial bearing insert 12. The mounting of the tibial bearing insert 12 to the tibial tray 14 is such that the tibial bearing insert is able to rotate with respect to the proximal or superior surface 32 of the tibial tray while remaining axially secured to the tibial tray.

The tibial bearing insert 12 has an anterior side 13, a posterior side 15, a superior articulation surface 16 and an inferior mating surface 18. The superior surface 16 may have one or more condylar elements 20 that are adapted to articulate with complementary condyle(s) of a femoral component (not shown) of a knee joint prosthesis. The inferior surface 18 preferably includes a mating stem 22 that protrudes from the inferior mating surface 18 and that is adapted to mate selectively with tibial tray 14.

The tibial tray 14 includes an anterior side 17, a posterior side 19, a superior mating surface 32 and an inferior bone contacting surface 34. The bone contacting surface 34 has a first portion 36 that represents an area of the inferior surface that mounts upon the proximal surface of a resected tibia (not shown). A second portion 38 of the bone contacting surface 34 extends from the first portion 36 and is adapted to extend into a cavity (not shown) formed within a patient's tibia. Preferably, the second portion 38 is an elongate tibial stem 39 that extends from the first portion 36. The tibial stem 39 has outer side and distal walls 40, 41. The outer side walls 40 of the tibial stem 39 may have irregular surface features (such as steps 42) to enhance bone fixation.

The superior surface 32 of the tibial tray 14 includes an aperture 72 (which may be of any suitable shape, e.g., substantially circular) that communicates with a mating cavity 44. In an illustrated embodiment, the mating cavity 44 is a blind cavity, defined by interior side walls 45 that extend into the tibial stem. The mating cavity 44 terminates in an interior distal wall 46 that may be substantially cone-shaped, or formed in another shape that is suitable for receiving a mating stem 22.

The mating stem 22 of the tibial bearing insert 12 is adapted to fit within the mating cavity 44 of the tibial tray. A securing mechanism ensures that the mating stem 22 is secured within the mating cavity 44 in such a way that the tibial bearing insert is axially secured to the tibial tray. Moreover, the tibial bearing insert must be able to rotate relative to the tibial tray while the two components are secured to one another.

One of ordinary skill in the art will readily appreciate that the dimensions of cavity 44 and mating stem 22 may vary. In one embodiment the cavity 44 has a diameter that tapers from proximal 51 to distal 53 ends thereof at an angle in the range of about 0.25° to 5°. The diameter at the proximal end 51 is in the range of about 5 to 40 mm and the diameter at the distal end 53 is in the range of about 3 to 39 mm. The cavity 44 preferably has a depth in the range of about 5 to 75 mm.

The mating stem 22 should have a size and shape complementary to the cavity 44. Accordingly, the diameter of stem 22 should taper from about 6 to 38 mm at a proximal end to about 3 to 30 mm a distal end. The length of stem 22 preferably is in the range of about 4 to 75 mm.

The superior surface 16 of the tibial bearing insert 12 may optionally include a blind bore 52 of the type illustrated in the embodiment of FIGS. 15–18. The blind bore 52 is substantially centrally located and is of a size and shape sufficient to receive a reinforcement pin 54 of the type shown in FIG. 19. Such reinforcement pins are well known in the art and may be substantially cylindrically shaped and made of a metal or metal alloy. Such pins may also have knurled or grooved surface features (not shown) as is known in the art. In one embodiment bore 52 is cylindrical, having a diameter of about 1 to 12 mm and a depth of about 5 to 75 mm.

Figure 29:
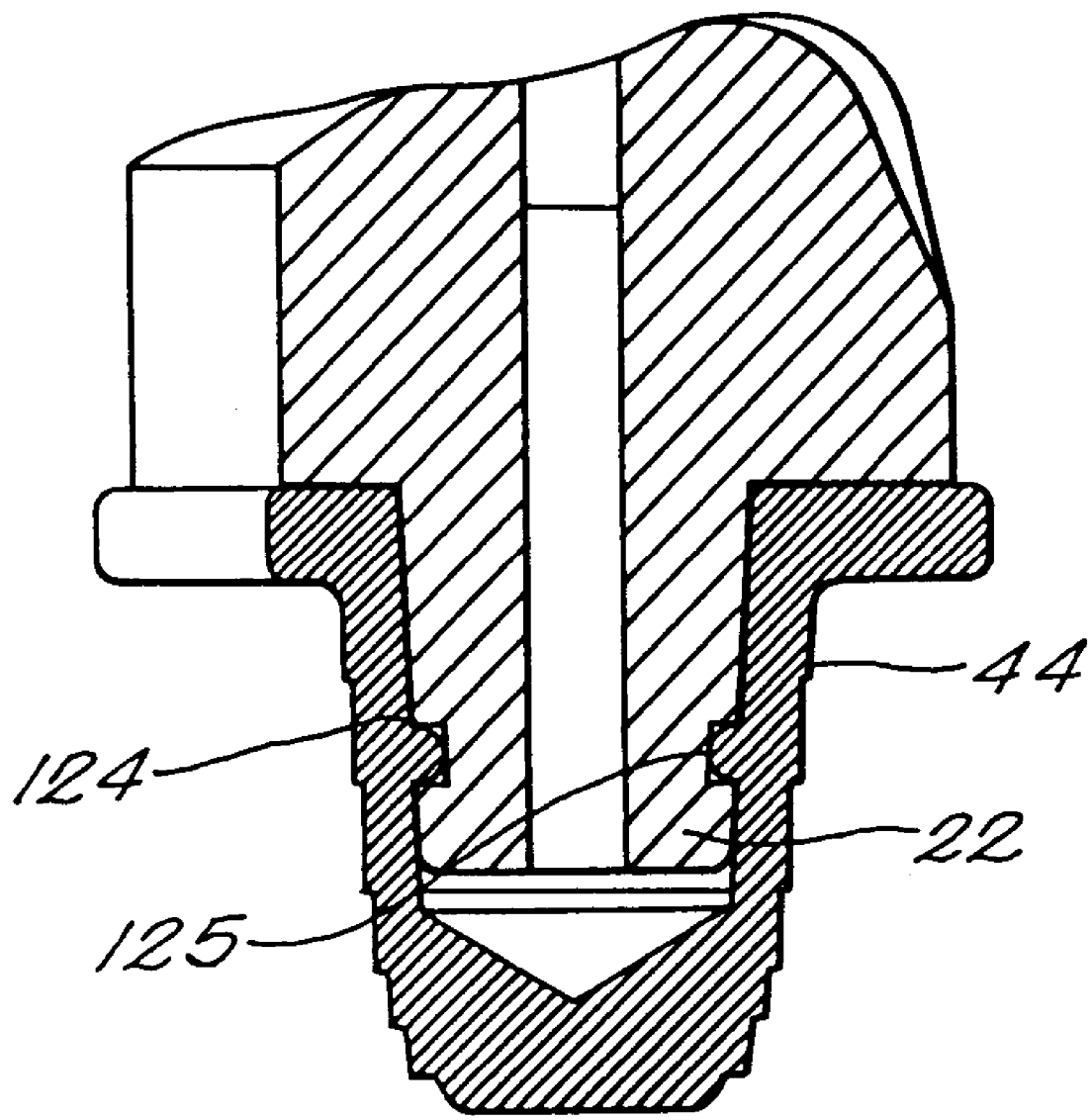
FIG. 29 is a sectional view of an alternative embodiment of a tibial component of a knee joint prosthesis system.

As shown in FIGS. 1–13, the securing mechanism of the tibial tray 14 and the tibial bearing insert 14 includes at least one negative surface feature 24 and at least one positive surface feature 26 which, upon engagement, form a snap fit arrangement that allows rotation of the second component with respect to the first component while axially securing the two components to each other. Preferably, the axial securement is sufficient to inhibit withdrawal of the tibial bearing insert 12 from the tibial tray 14 when a separating force, e.g., an upwardly-directed force, acts on the tibial bearing insert 12. Although the tibial bearing insert is shown to include a negative surface feature while the tibial tray includes a positive surface feature, it is understood that this arrangement can be reversed so that the positive surface feature is present on the tibial tray and the negative surface feature is present on the tibial bearing insert. For example, FIG. 29 illustrates a positive surface feature 124 formed within mating cavity 44 and a negative surface feature 125 formed on mating stem 222.

The negative surface feature 24 may be in the form of one or more grooves 28 formed in mating cavity 44. Grooves 28 may be formed in the cavity 44 at the proximal end 51, distal end 53, or at intermediate locations. In one embodiment, separate grooves 28 are formed on each of the anterior and posterior sides of mating cavity 44. Each groove 28 is in the form of an arc that extends along a portion of the perimeter of the mating cavity 44. Preferably, each groove forms an arc of about 5° to 60°.

Each groove 28 is defined by a first vertical surface 56, a horizontal shoulder 58, recessed vertical surface 60 and a bottom surface 62. The horizontal shoulder 58 may extend from the recessed vertical surface 60 at an angle of between about 45° and 90°, and most preferably at an angle of 90°. The length ($L_1$) of horizontal shoulder 58, which is the distance by which the recessed vertical surface 60 is offset from the first vertical surface 56, should be sufficient to ensure and maintain engagement of the positive surface features 26 with the grooves 28. Preferably, this length ($L_1$) is about 0.25 to 3.00 mm.

One of ordinary skill in the art will appreciate the height (H) of recessed vertical surface 60 may vary depending upon the requirements of a given application. In any event, this height must be sufficient to accommodate the positive surface features. As described below, the height need not be constant. Instead, the height can taper from a maximum height ($H_{max}$) at a central portion 30 of the groove to a minimum height ($H_{min}$) at end portions 31 of the groove. The use of a groove having a tapered height can gradually restrict rotational movement of the tibial bearing insert 12.

As noted above, at least one groove 28 is disposed on the tibial tray. The groove(s) may be present on any part of the tibial tray, as long as they are able to engage with a corresponding positive surface feature on the tibial bearing insert. The groove(s) preferably are located within the mating cavity 44, on either the inner side walls 45 or the distal wall thereof. In an embodiment illustrated in FIGS. 1 to 13, the grooves are located at a proximal end of mating cavity 44.

Although only one, continuous groove may be used, it is preferable to utilize two opposed grooves. For purposes of illustration, grooves 28 are shown to be on opposed anterior 17 and posterior 19 sides of the tibial tray 14. It is understood, however, that opposed grooves may instead be disposed on other locations of the tibial tray, including on medial and lateral sides of the tibial tray.

One of ordinary skill in the art will readily appreciate that suitable negative surface features may include structures other than the grooves described herein.

Positive surface features 26 include virtually any structures protruding from the tibial bearing insert 12 that are able to mate with the negative surface features 24 (e.g., grooves 28) of the tibial tray 14 to enable the tibial bearing insert 12 to rotate with respect to the tibial tray 14 and to axially secure these components to each other.

Referring to FIGS. 1 to 13 the system 10 includes at least one positive surface feature, each of which includes protruding members that are formed on a portion of the tibial bearing insert 12 such that they are able to mate with grooves. In one embodiment each positive surface feature is a snap member 64, which may be slightly deformable or deflectable, that forms an arc over a portion of the surface of the tibial bearing insert 12. Each snap member 64 forms an arc that is smaller than the corresponding arc of groove 28 with which it is to engage, in order to facilitate rotation of the tibial bearing insert 12 with respect to the tibial tray 14 when the grooves 28 and snap members 64 are mated. The arc formed by the snap members 64 should be about 5° to 90° less than that of grooves 28. Preferably, the snap members 64 form an arc of 4° to 85°.

For purposes of illustration, the snap member 64 is shown to be formed on a portion of the inferior surface 18 of the tibial bearing insert 12 that is in proximity to the mating cavity 44. It is understood, however, that the snap member may be disposed at alternative locations on tibial bearing insert 12.

As shown in FIGS. 4, 7 and 11, each snap member may include a cantilevered wall 66 that extends from the tibial bearing insert 12. A distal end 68 of cantilevered wall extends radially outwardly from wall 66 and has a radius wall 70 and an engaging shoulder 74. In an illustrated embodiment, the cantilevered wall 66 extends vertically downwardly from inferior surface 18 and the engaging shoulder 74 has a horizontal surface 76 that is orthogonal to the cantilevered wall 66. The cantilevered wall 66 preferably is separated from the adjacent surface 65 of mating stem 22 by a distance of about 0.25 to 3.00 mm.

One of ordinary skill in the art will appreciate that the dimensions of snap member may vary. Generally, however, the cantilevered wall 66 has a length of about 0.25 to 3.00 mm. The horizontal surface 76 of the engaging shoulder 74 preferably extends over a distance of about 0.25 to 3.00 mm. The radius wall 70 should have sufficient curvature to promote the mating of the snap members 84 within groove 28. In one embodiment, the radius wall 70 has a radius in the range of about 0.10 mm to 1.00 mm.

The system 10 is assembled by forcing the tibial bearing insert 12 within the tibial tray 14. As the radius wall 70 contacts the tibial tray 14 and as force is applied to the tibial bearing insert 14 radius wall 70 slides past the first vertical surface 56 of groove 28. In one embodiment, the cantilevered wall 66 of the snap member 64 deflects by a minimal amount sufficient to accommodate the mating of the snap member and the groove. Once the snap member is fully inserted within the groove, the cantilevered wall 66 returns to its original position and the horizontal surface 76 of the engaging shoulder 74 of the snap member abuts the horizontal shoulder 58 of the groove, thereby providing axial securement of the tibial bearing insert 12 to the tibial tray 14.

At the same time, some degree of rotation of the tibial bearing insert with respect to the tibial tray is possible because the arc defined by the grooves is greater than the arc defined by the snap members. Preferably, the tibial bearing insert is able to rotate in the range of about 1° to 30°.

Figure 12:
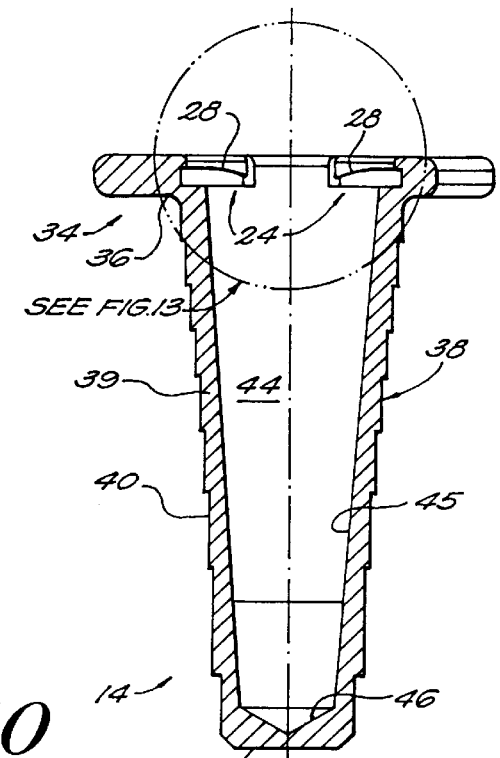
FIG. 12 is a side sectional view of an alternative embodiment of the invention in which tapered negative surface features are formed in the tibial tray.
Figure 13:
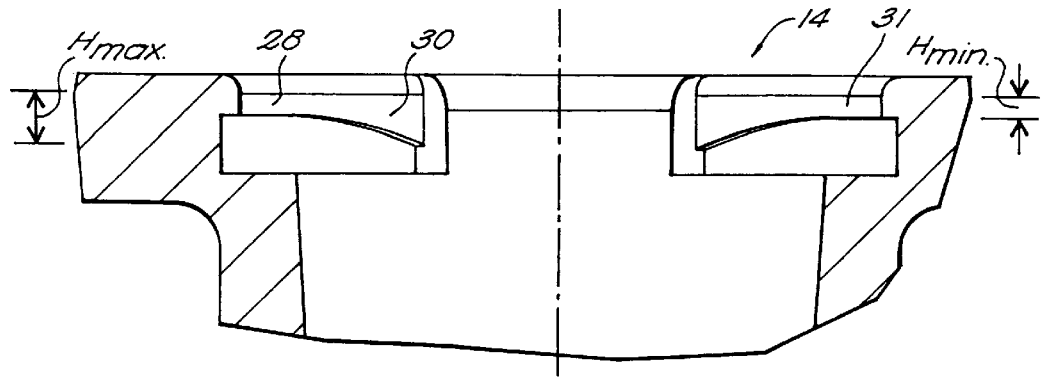
FIG. 13 is a detail view of portion "C" of the tibial tray of FIG. 8.
Figure 14:
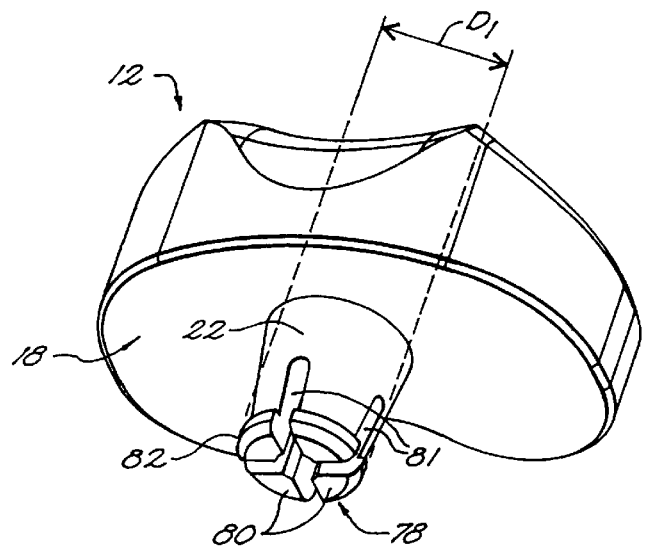
FIG. 14 is a perspective view of an alternative tibial bearing insert useful with the present invention.
Figure 15:
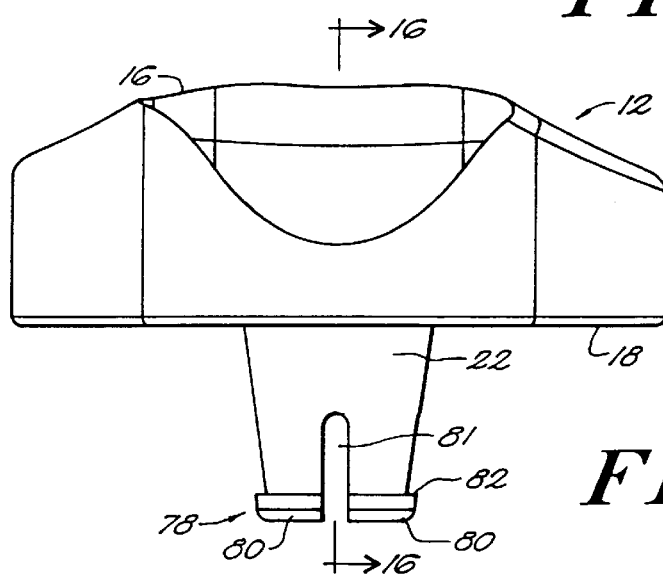
FIG. 15 is a front view of the tibial bearing insert of FIG. 14.
Figure 16:
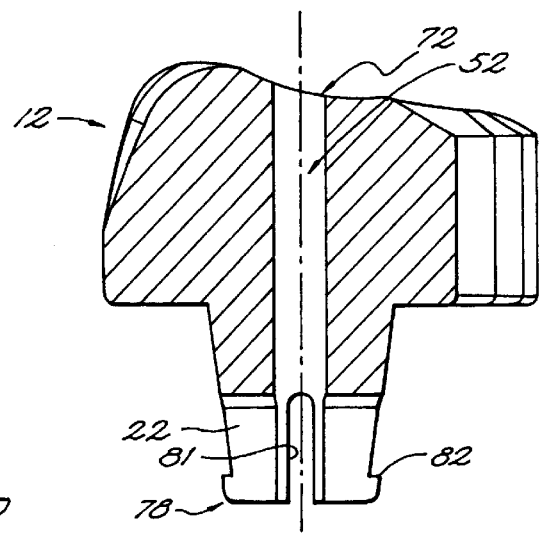
FIG. 16 is a side sectional view of the tibial bearing insert of FIG. 15, at line 16—16.

In one embodiment, shown in FIGS. 12 and 13, the grooves 28 may have a height that tapers from a maximum height ($H_{max}$) at a central portion 30 of the groove 31 to a minimum height ($H_{min}$) at end portions of the groove. By way of example, the maximum height may be about 0.25 mm and the minimum height may be about 30 mm. The use of a tapered groove can be advantageous as it allows increasing resistance to rotation, thereby gradually restricting rotation.

One of ordinary skill in the art will appreciate that each snap member should have dimensions suitable to enable it to fit snugly within grooves 28 with substantially no axial play. The fit of the snap members within the grooves should not be so snug, however as to present excess friction upon rotation of the tibial bearing insert. If desired a seal member (not shown) may be disposed within grooves 28 to reduce axial play and or radial movement.

It is understood that the negative and positive surface features may be disposed at any location on the tibial bearing insert 12 and tibial tray 14 that enables these surface features to be suitably engaged with each other to properly orient the tibial bearing insert 12 with respect to the tibial tray 14. In one embodiment, at least two positive surface features are present on the tibial bearing insert, at locations opposite one another.

Figure 17:
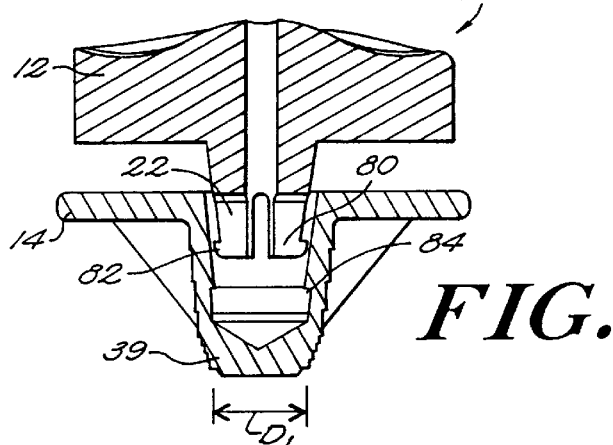
FIG. 17 is a front sectional view of a prosthesis system utilizing the tibial bearing insert of FIG. 16, with the tibial bearing insert unsecured within the tibial tray.
Figure 18:
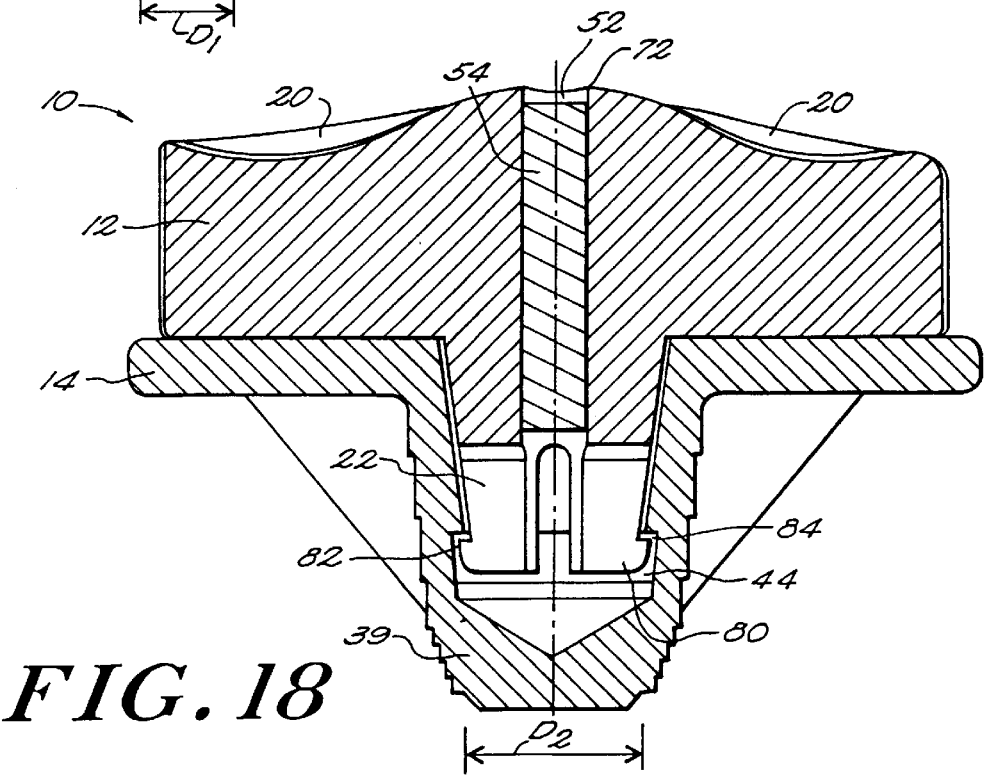
FIG. 18 is a front sectional view of the prosthesis system of FIG. 17, with the tibial bearing insert secured within the tibial tray.

One of ordinary skill in the art will appreciate that the securing mechanism of the tibial tray and the tibial bearing insert (or any other joint system of the invention) may be modified by any structure that facilitates the axial securement of the tibial bearing insert to the tibial tray while preserving rotatability of the tibial bearing insert. FIGS. 14–18 illustrate an embodiment in which the distal end 78 of the mating stem 22 includes positive surface features in the form of expandable wedge-like elements 80, each of which is separated by a slot 81. Each wedge-like element 80 has a protruding shoulder 82 on an exterior surface thereof. The expandable wedge-like elements 80, in cooperation with slots 81, enable the diameter of the distal end 78 of the mating stem 22 to expand from a first diameter ($D_1$) to a second diameter ($D_2$). The first diameter ($D_1$), as shown in FIG. 17, is insufficient to enable the protruding shoulders 82 of the wedge-like members 80 to engage a corresponding negative surface feature (e.g., groove 84) in mating cavity 44. However expansion of the mating stem 22 to the second diameter ($D_2$), as shown in FIG. 18, causes interaction between the protruding shoulders 82 and the groove 84 that prevents removal of the tibial bearing insert 12 from the tibial tray 14. Despite this axial securement, the tibial bearing insert 12 is still able to rotate relative to the tibial tray 14.

The expansion of the mating stem from the first diameter to the second diameter may be accomplished by the insertion of a reinforcement pin 54 within a blind bore 52 formed in the superior articulation surface 16 of the tibial bearing insert 12. The mating of pin 54 within bore 52 causes expansion of the distal end of the mating stem from the first to the second diameter.

The reinforcement pin 54 may be of the type described above and shown in FIG. 19. The blind bore 52 is preferably located substantially centrally on the superior articulation surface 16 of the tibial bearing insert 12 and is of a size and shape sufficient to receive a reinforcement pin 54. In one embodiment, the bore 52 is cylindrical and has a diameter of about 1 to 12 mm and a depth of about 12 to 76 mm. The reinforcement pin may have a diameter of about 1 to 10 mm and a length of about 5 to 60 mm.

FIGS. 14–18 illustrate four wedge-like elements 80 formed at the distal end 78 of mating stem 22. It is understood, however, that an alternative number of wedge elements 80 may be present. For example, mating stem 22 may have only two or three wedge elements, or more than four.

Alternatively, the tibial bearing insert 12 may include wedge-like elements 80 that are biased to a first diameter that enables axial securement with tibial tray 14. Upon mating of the tibial bearing insert 12 with tibial tray 14, the wedge-like elements are compressed to a second, smaller diameter. Upon proper seating of the tibial bearing insert the wedge-like elements return to the first diameter.

The embodiment of FIGS. 14–18 may be further modified by omitting wedge-like elements 80 and groove 84. Instead axial securement can be provided by the frictional engagement of mating stem 22 with the inner wall of mating cavity 44 when reinforcement pin 54 is inserted into bore 52. Surface features (not shown) analogous to wedge-like elements 80 may be provided at a proximal portion of mating stem 22 to interact with complementary surface features on a top portion of cavity 44 when the reinforcement pin 54 is inserted. The surface features on the mating stem 22 can be of dimensions smaller than the surface features on the cavity 44 so as to limit the degree of rotation of the tibial bearing insert 12.

Figure 27:
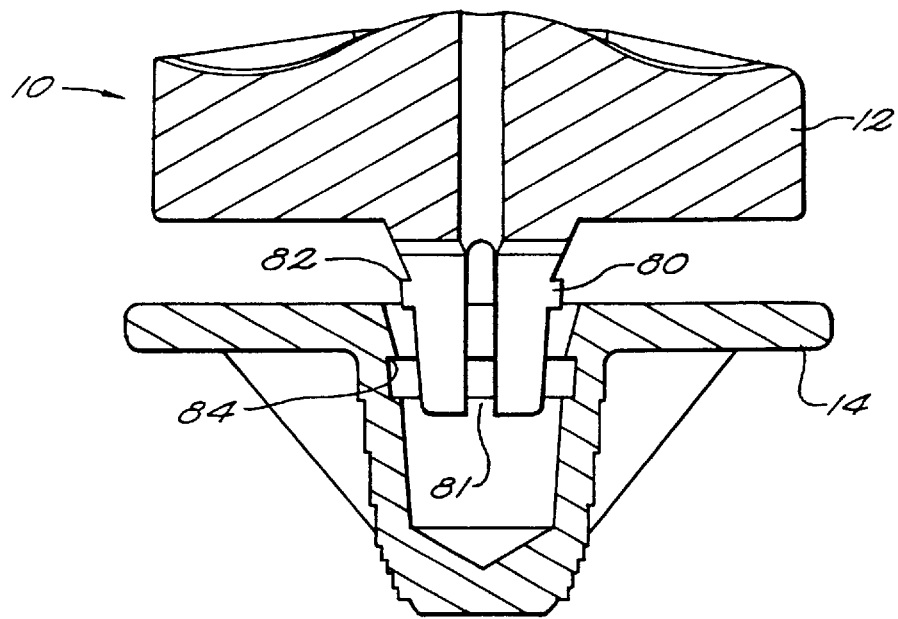
FIG. 27 is a sectional view of an unassembled alternative prosthesis system according to the invention.
Figure 28:
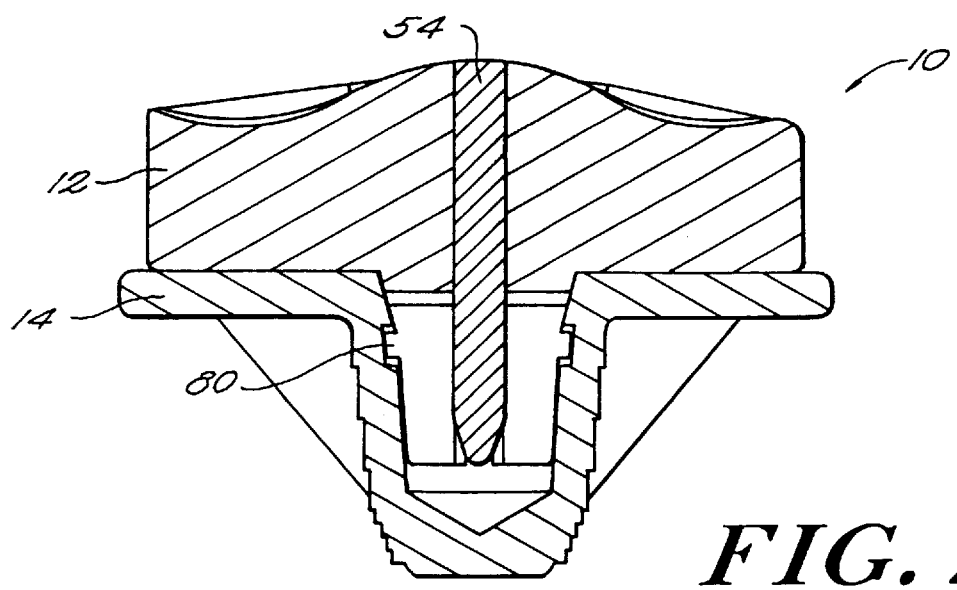
FIG. 28 is a sectional view of the prosthesis system of FIG. 27 in an assembled condition.

FIGS. 27 and 28 illustrate an alternative embodiment in which wedge-like elements 80 are disposed at a more proximal portion of mating stem 22.

FIGS. 20–26 illustrate an alternative securing mechanism for the tibial tray 14 and the tibial bearing insert 12 that includes at least one negative surface feature 85 and at least one positive surface feature 87, that are matable to axially secure the tibial bearing insert 12 to the tibial tray 14 while permitting rotation of the tibial bearing insert 12 with respect to the tibial tray 14. Although the tibial tray is shown to include a negative surface feature 85 while the tibial bearing insert includes a positive surface feature 87, it is understood that this arrangement can be reversed.

The negative surface feature 85 may be in the form of at least one circumferential groove 90 that extends partially or entirely around the perimeter of the mating cavity 44. The circumferential groove 90 may extend in a linear fashion about the interior side walls 45 of fashion about the perimeter of mating cavity 44, or it may follow another path, such as an eccentric, sinusoidal, parabolic, or wave. Further, the circumferential groove(s) may be present at any location on the tibial tray, as long as it is able to engage with a corresponding positive surface feature on the tibial bearing insert 12. The circumferential groove(s) preferably are disposed on the inner side walls 45 of the mating cavity 44. Circumferential groove 90 may be located at any position between the proximal and distal ends 51, 53 of mating cavity 44.

The dimensions of circumferential groove(s) 90 may vary within limits readily appreciated by one of ordinary skill in the art. The circumferential groove 90 may have a substantially constant opening width (W) in the range of about 1 to 20 mm. The depth of circumferential groove 90 generally is in the range of 0.25 to 2.00 mm.

One of ordinary skill in the art will readily appreciate that suitable negative surface features may include structures other than the circumferential groove described herein.

Positive surface feature 87 also includes virtually any structure that protrudes from the tibial bearing insert 12 that is able to mate with the negative surface feature 85 (e.g., the circumferential groove 90) of the tibial tray 14 to enable the tibial bearing insert 12 to rotate with respect to the tibial tray 14 and to axially secure these components to each other.

As shown in FIGS. 20–26, the positive surface feature 87 is in the form of an eccentric rib 86 that extends over a portion of the surface of the tibial bearing insert 12. The term "eccentric rib" refers to the property of the rib 86 that enables it to form a substantially sinusoidal, parabolic, or wave-like path about all or part of the outer surface of mating stem 22. Preferably, the difference between high and low points in the oscillation of rib 86 is about 1 to 10 mm. The rib 86 may extend about the circumference of the mating stem 22 over a range of about 1 to 4 oscillation cycles.

The dimensions of rib 86 may also vary and depend to a large extent on the dimensions of the circumferential groove 90. The rib 86 must be of dimensions that enable it to fit within circumferential groove 90 to axially secure tibial bearing insert 12 to tibial tray 14. There must also exist sufficient clearance to enable some side-to-side movement of the rib 86 within circumferential groove 90 to permit some rotation of the tibial bearing insert 12. The rib 86 must also have a thickness (T) that is less than the width (W) of circumferential groove 90. Generally, the thickness (T) of rib 86 ranges between about 1 and 15 mm. The eccentric rib 86 should protrude from mating stem 22 by a distance that is less than the depth circumferential groove 90.

The eccentric rib 86 may be disposed at various locations on tibial bearing insert 12. Preferably, however, the eccentric rib 86 is formed on a surface of mating stem 22. Such that it extends partially or fully about the circumference of mating stem 22.

Upon mating of rib 86 within circumferential groove 90, the tibial bearing insert 12 and tibial tray are axially secured to each other. The tibial bearing insert 12 is also able to rotate with respect to the tibial tray 14. However, the degree of rotation is generally limited to about 5° to 90°. As rotation progresses the high point 102 and/or low point 104 of rib 86 impinges upon the walls of the groove, prohibiting further rotation, or greatly increasing the force necessary to effect rotation. In one embodiment, the rib 86 and groove 90 are generally of the same shape.

One of ordinary skill in the art will appreciate that the rotation of the tibial bearing insert may further be controlled by varying other dimensions of the circumferential groove 90 and/or the eccentric rib 86, such as the length of the eccentric rib, the distance by which the eccentric rib extends into the circumferential groove, and the width of the circumferential groove.

Figure 23:
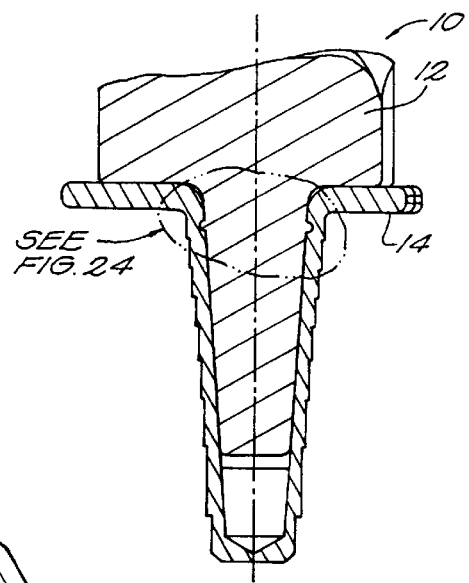
FIG. 23 is a sectional view at lines 23—23 of the prosthesis system of FIG. 22.
Figure 24:
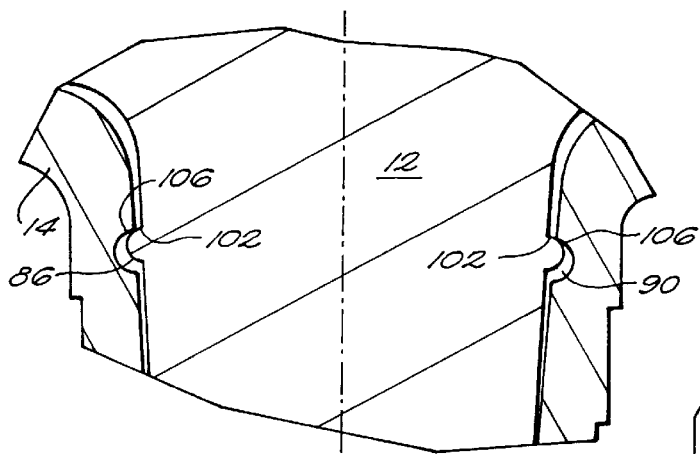
FIG. 24 is a view of the Detail A of FIG. 23.
Figure 25:
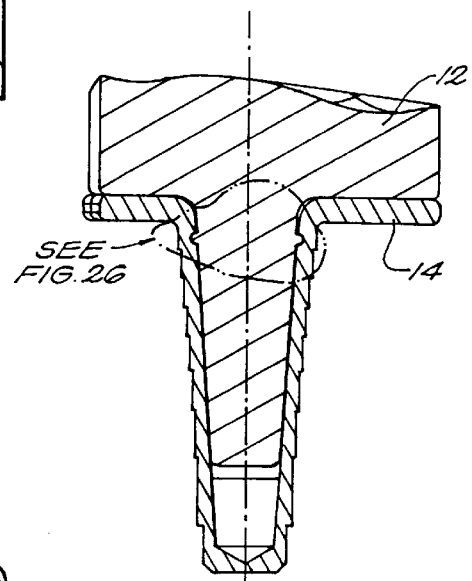
FIG. 25 is a sectional view at lines 25—25 of the prosthesis system of FIG. 22.
Figure 26:
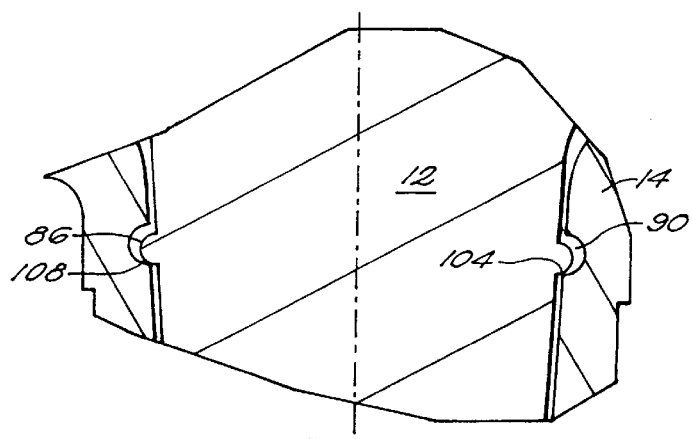
FIG. 26 is a view of Detail B of FIG. 25.

FIGS. 22 through 26 illustrate the ability of groove 90 and rib 86 to limit rotation of tibial bearing insert 12. In FIG. 22, the tibial bearing insert is rotated by approximately 5°. Upon doing so, the high points 102 of rib 86, as shown in FIGS. 23 and 24, impinge upon upper walls 106 of groove 90, thereby preventing further rotation, or greatly increasing the force necessary to effect further rotation. At the same time, as shown in FIGS. 25 and 26, the low points 104 of rib 86 impinge upon lower walls 108 of groove 90.

One of ordinary skill in the art will appreciate that the components of the system 10 of the invention can be made from a variety of known materials. The tibial bearing insert typically is made of a polymeric material such as ultra high molecular weight polyethylene. The tibial bearing insert can be made of a variety of known metals and metal alloys that are suitable for implantable prostheses.

One of ordinary skill in the art will further appreciate that minor modifications may be made to the invention described herein without departing from its intended scope. All references noted herein are expressly incorporated by reference in their entirety.

What is claimed is:

1. A joint prosthesis system, comprising:
   a first component having a superior mounting surface and an inferior bone contacting surface, the superior mounting surface having a cavity defined by inner side and distal walls;
   a second component, rotatable with respect to the first component, having a superior articulation surface, an inferior mating surface and a mating stem protruding from the inferior mating surface, wherein the mating stem is integrally formed of the same material from which the second component is formed;
   a securing mechanism comprising at least one groove formed in one of the cavity of the first component and the mating stem of the second component, and at least one eccentric rib formed on and protruding from a surface of the other of the cavity of the first component and the mating stem of the second component, the at least one groove and the at least one eccentric rib being matable with each other upon mounting of the second component within the first component to provide positive axial securement of the second component relative to first component and to enable rotation of the second component relative to the first component.

2. The system of claim 1, wherein the at least one groove extends around an entire circumference of a portion of the cavity.

3. The system of claim 2, wherein the at least one eccentric rib extends around the entire circumference of a portion of the mating stem.

4. The system of claim 1, wherein the at least one groove follows a substantially sinusoidal path about a circumference of the cavity.

5. The system of claim 4, wherein the at least one eccentric rib follows a substantially sinusoidal path about the circumference of the mating stem.

6. The system of claim 5, wherein the sinusoidal path followed by the at least one eccentric rib has maximum and minimum points and the distance between the maximum and minimum points is in the range of about 1 to 10 mm.

7. The system of claim 6, wherein the sinusoidal path of the at least one eccentric rib has a period in the range of about 1 to 4 oscillation cycles.

8. The system of claim 4, wherein the sinusoidal path followed by the at least one groove has maximum and minimum points and the distance between the maximum and minimum points is in the range of about 1 to 10 mm.

9. The system of claim 8, wherein the sinusoidal path of the groove has a period in the range of about 1 to 4 oscillation cycles.

10. The system of claim 1, wherein the at least one groove has a depth in the range of about 0.25 to 2 mm.

11. The system of claim 10, wherein the at least one eccentric rib protrudes from the mating stem by a distance in the range of about 0.25 to 2 mm.

12. The system of claim 11, wherein the at least one eccentric rib has a thickness in the range of about 1 to 20 mm.

13. The system of claim 12, wherein the at least one groove has a width in the range of about 1 to 20 mm.

14. The system of claim 13, wherein the relative dimensions of the at least one groove and the at least one eccentric rib are such that the second component may rotate relative to the first component over a range of 5° to 90°.

15. The system of claim 1, wherein the first component comprises a tibial tray.

16. The system of claim 1, wherein the second component comprises a tibial bearing insert.

* * * * *